United States Patent
Kear et al.

(10) Patent No.: US 7,731,723 B2
(45) Date of Patent: *Jun. 8, 2010

(54) MEDICAL RETRIEVAL DEVICE

(75) Inventors: Jason W. Kear, Bloomington, IN (US); Justin Reppert, Spencer, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/730,527

(22) Filed: Apr. 2, 2007

(65) Prior Publication Data

US 2007/0179517 A1    Aug. 2, 2007

Related U.S. Application Data

(63) Continuation of application No. 10/273,513, filed on Oct. 18, 2002, now Pat. No. 7,211,089.

(51) Int. Cl.
    *A61B 17/22*    (2006.01)
(52) U.S. Cl. ..................................................... 606/127
(58) Field of Classification Search .................. 606/113, 606/114, 127, 151, 157, 200, 210
See application file for complete search history.

(56) References Cited

U.S. PATENT DOCUMENTS

| | | | |
|---|---|---|---|
| 3,805,791 A | 4/1974 | Seuberth et al. | |
| 4,174,715 A | 11/1979 | Hasson | |
| 4,611,594 A | 9/1986 | Grayhack et al. | |
| 4,655,219 A | 4/1987 | Petruzzi | |
| 5,098,440 A * | 3/1992 | Hillstead | 606/108 |
| 5,569,274 A * | 10/1996 | Rapacki et al. | 606/151 |
| 5,653,716 A | 8/1997 | Malo et al. | |
| 5,924,175 A | 7/1999 | Lippitt et al. | |
| 5,944,728 A | 8/1999 | Bates | |
| 6,090,129 A | 7/2000 | Ouchi | |
| 6,203,552 B1 | 3/2001 | Bagley et al. | |
| 6,350,266 B1 | 2/2002 | White et al. | |
| 6,368,328 B1 | 4/2002 | Chu et al. | |
| 6,506,209 B2 * | 1/2003 | Ouchi | 606/206 |
| 7,087,062 B2 * | 8/2006 | Dhindsa | 606/127 |

* cited by examiner

*Primary Examiner*—Kevin T Truong
(74) *Attorney, Agent, or Firm*—Finnegan, Henderson, Farabow, Garrett & Dunner

(57) ABSTRACT

A medical retrieval device has a multi-prong retrieval assembly. The multi-prong retrieval assembly has a first position, in which the retrieval assembly extends from the distal end of the sheath to form an open ended grasping device, and a second position, in which the retrieval assembly extends from the distal end of the sheath to form a substantially close ended basket-type retrieval device. When the retrieval assembly is used as a basket-type retrieval device, the distal ends of the prongs of the retrieval assembly that form the basket are not connected to each other. Thus, captured objects may be released by the operator, or by applying sufficient force to separate one or more of the prongs.

19 Claims, 6 Drawing Sheets

MEDICAL RETRIEVAL DEVICE

This is a continuation of application Ser. No. 10/273,513, filed Oct. 18, 2002 now U.S. Pat. No. 7,211,089, the entire disclosure of which is incorporated herein by reference.

TECHNICAL FIELD

The invention generally relates to medical devices for retrieving material from within a body. More particularly, the invention relates to a medical retrieval device that combines the functions of grasper-type retrieval devices and basket-type retrieval devices.

BACKGROUND

Blockages or obstructions, such as stones or calculi can develop in certain parts of the body, including the kidneys, pancreas, esophagus, and gallbladder. Minimally invasive surgical procedures, typically involving percutaneous insertion of a retrieval device through an endoscope or laparoscope, may be used to break up and remove such blockages. For example, currently available medical retrieval devices provide physicians with the ability to retrieve stones that are in easily accessible areas of the urinary tract.

One type of retrieval device, known as a "basket" retrieval device, typically is formed of a wire assembly that surrounds a captured stone or calculi during retrieval. Many known basket-type devices collapse into the distal end of a catheter during insertion, and are extended from the end of the catheter when deployed. Basket-type retrieval devices typically require a physician to advance the device past the stone mass, deploy the retrieval device, and then pull it back toward the stone to capture the stone.

Difficulties can arise when using such a basket device when, for example, a stone becomes stuck or wedged during removal. In such a situation, damage to surrounding tissue or tissue lining may result if the physician forces the basket and stone through an area in which the stone has become stuck or wedged. To avoid such damage, it may be necessary to release the stone and break it into smaller fragments. Unfortunately, typical basket retrieval devices do not allow the physician to release easily the stone and continue breaking it up before removal is again attempted.

To address these difficulties, stone removal can be accomplished using a grasper, instead of a basket device. Typically, a grasper is a device having three or four prongs that are manipulated to capture a stone from the front side of the stone, by grasping it. When a stone becomes stuck or wedged during removal, such graspers are able to release the stone. Unfortunately, graspers typically do not hold on to stones as well as baskets. It may be difficult to capture a stone using a grasper, and once captured, it is easy for the stone to be released inadvertently.

Over the course of a procedure, a physician may need to use both graspers and basket-type devices to manipulate a stone, break up the stone, and remove fragments of the stone. Using current graspers and baskets, a physician may need to switch devices during the procedure. Switching devices typically requires withdrawal of one device and insertion of another.

SUMMARY OF THE INVENTION

The invention generally relates to a single medical retrieval device that can function as both a grasper and a basket-type retrieval device. A combined grasper and basket device according to the invention can easily grasp, release, and transport stones or other calculi.

In one aspect, the invention involves a medical retrieval device that comprises a sheath and a multi-prong retrieval assembly. The multi-prong retrieval assembly has a first position, in which the multi-prong retrieval assembly extends from a distal end of the sheath to form an open ended grasping device, and a second position, in which the multi-prong retrieval assembly extends from the distal end of the sheath to form a substantially close ended basket-type retrieval device.

In one embodiment, the open-ended grasping device is adapted to capture material by grasping a front portion of the material. The substantially close-ended basket-type retrieval assembly is adapted to capture material by enclosing the material within the basket-type retrieval device.

In one embodiment, a portion of the multi-prong retrieval assembly is exposed to form the open ended grasping device when the multi-prong retrieval assembly is in the first position. Substantially the entire multi-prong retrieval assembly is exposed to form the substantially close ended basket-type retrieval device when the multi-prong retrieval assembly is in the second-position.

In one embodiment, a prong of the multi-prong retrieval assembly has a barbed tip. The barbed tip may be oriented to face a central, or longitudinal axis of the retrieval assembly when the retrieval assembly is in the first position.

In one embodiment, a prong of the multi-prong retrieval assembly has a rolled tip.

In one embodiment, one or more teeth are disposed on a distal portion of the multi-prong retrieval assembly that extends from the sheath when the retrieval assembly is in the first position. These teeth may be oriented to face a central or longitudinal axis of the retrieval assembly when the retrieval assembly is in the first position.

In one embodiment, one or more prongs of the multi-prong retrieval assembly are deformable, such that the distal ends of the prongs may separate from each other to release a captured object when the retrieval assembly is in the second position and a predetermined force is applied to the prongs.

In one embodiment, the medical retrieval device may be actuated to cause the prongs of the multi-prong retrieval assembly to separate from each other when the retrieval assembly is in the second position.

Certain embodiments of the medical retrieval device include a retrieval assembly having either three or four prongs, though other embodiments may include a greater number of prongs. Generally, a prong of the retrieval assembly may be composed of nitinol, stainless steel, a Co—Cr alloy, or a titanium alloy, though other materials also may be used.

In another aspect of the invention, in use, a portion of the medical retrieval device is inserted into a body tract while the multi-prong retrieval assembly is in a collapsed position within the sheath. The multi-prong retrieval assembly is then placed in a position in which it extends from the distal end of the sheath, and maneuvered to capture material. Once the material is captured, the medical retrieval device, along with the material are withdrawn from the body.

The multi-prong retrieval assembly may be placed in a first position, permitting the device to be used as a grasper, for grasping material similar to forceps. The multi-prong retrieval assembly also may be placed in a second position, permitting the device to be used as a basket-type retrieval device to capture material within a basket formed by the prongs of the multi-prong retrieval assembly. If necessary, the material may be released from the device by applying force to one or more of the prongs or the multi-prong retrieval assembly. Material may also be released by actuating the medical retrieval device to open the multi-prong retrieval assembly.

In another aspect of the present invention, a multi-position medical retrieval device may be deployed by placing a multi-prong retrieval assembly in a first position, in which the multi-prong retrieval assembly extends from a distal end of a sheath to form an open ended grasping device, and by placing the multi-prong retrieval assembly in a second position, in which the multi-prong retrieval assembly extends from the distal end of the sheath to form a substantially close-ended basket-type retrieval device. The multi-prong retrieval assembly may also be placed into a collapsed position within the distal end of the sheath.

In one embodiment, deploying the multi-position medical retrieval device further comprises actuating the multi-position medical retrieval device when the multi-prong retrieval assembly is in the first position to open or close the open ended grasping device formed by the multi-prong retrieval assembly.

In one embodiment, deploying the multi-position medical retrieval device further comprises actuating the multi-position medical retrieval device when the multi-prong retrieval assembly is in the second position to open the substantially close-ended basket-type retrieval device formed by the multi-prong retrieval assembly.

These and other objects, advantages, and features of the invention will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWING

In the drawings, like reference characters generally refer to the same parts throughout the different views. The drawings are not necessarily to scale, emphasis instead generally being placed upon illustrating the principles of the invention. In the following description, various embodiments of the present invention are described with reference to the following drawings, in which.

DESCRIPTION

Figure 1A:
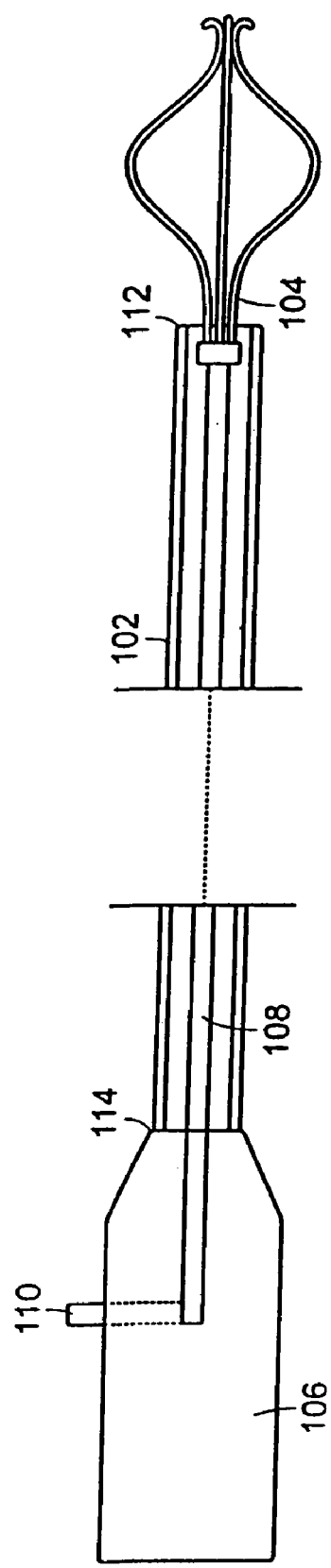
FIGS. 1A-B show illustrative embodiments of a medical retrieval device constructed in accordance with the invention.

FIG. 1A shows a view of a medical retrieval device 100 in accordance with an illustrative embodiment of the present invention. The medical retrieval device 100 includes a sheath 102, a retrieval assembly 104, disposed at a distal end 112 of the sheath 102, and a handle 106, disposed at a proximal end 114 of the sheath 102. As shown in FIG. 1A, the retrieval assembly 104 is in an extended position, in which the retrieval assembly 104 extends from the distal end 112 of the sheath 102. The retrieval assembly 104 may be placed in this extended position either by pushing the retrieval assembly 104 out of the distal end 112 of the sheath 102, or by retracting the distal end 112 of the sheath 102 to expose a portion of the retrieval assembly 104.

An elongated member 108 extends within the sheath 102 from an actuating mechanism 110 on the handle 106 to the retrieval assembly 104. Operation of the actuating mechanism 110 can move the elongated member 108 to cause the retrieval assembly 104 to be placed in a collapsed position within the sheath 102, or to extend from the distal end 112 of the sheath 102 into a first position, in which the retrieval assembly 104 is used as a grasper, or into a second position, in which the retrieval assembly 104 is used as a basket-type retrieval device.

Figure 1B:
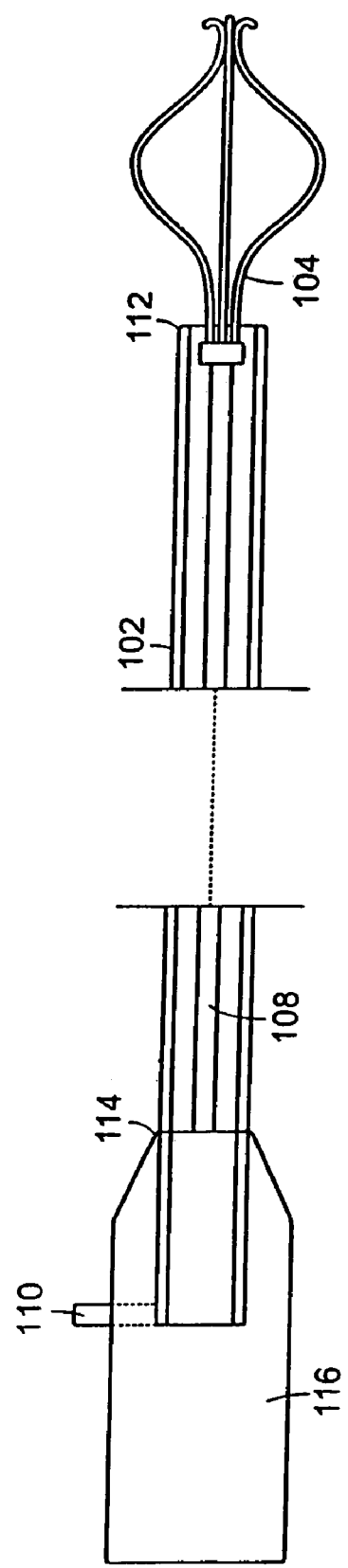

Alternatively, as shown in FIG. 1B, the actuating mechanism 110 can cause movement of the sheath 102, while the elongated member 108 is connected to the handle 106, and remains stationary. The actuating mechanism 110 can advance the sheath 102 over the retrieval assembly 104 (which remains stationary), to enclose the retrieval assembly 104 in a collapsed position within the sheath 102. Similarly, the actuation mechanism 110 can move the sheath 102 back, while the retrieval assembly 104 remains stationary, so that at least a portion of the retrieval assembly 104 extends beyond the distal end 112 of the sheath 102, placing the retrieval assembly 104 into the first or second positions.

It will be understood that the sheath 102, the retrieval assembly 104, the handle 106, the elongated member 108, and the actuating mechanism 110 as illustrated in FIG. 1 are not shown in their correct size or proportion to each other. The sheath 102 is dimensioned to fit the requirements of its application in the body. For example, for urological applications, the diameter of the sheath 102 is typically between 1.7 and 8.0 french, though some applications may call for larger or smaller sizes.

Figure 2A:
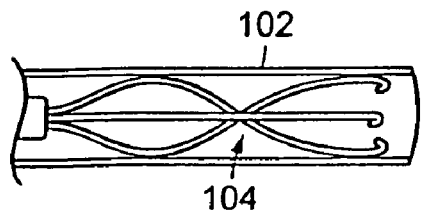
FIGS. 2A-C show an embodiment of a retrieval assembly in accordance with the invention in a collapsed position, a first position, and a second position, respectively.
Figure 2B:
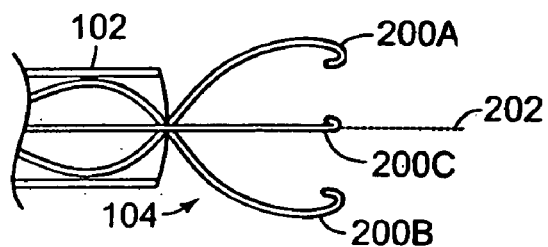
Figure 2C:
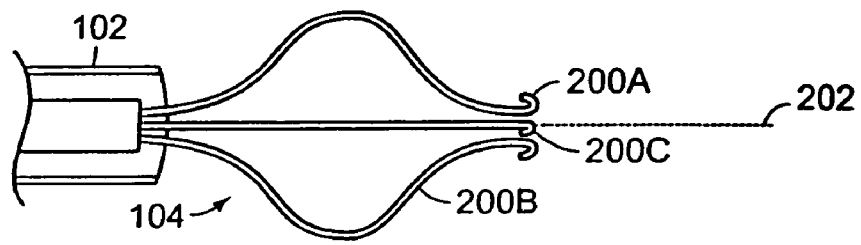

Referring now to FIGS. 2A-C, the retrieval assembly 104 is described in greater detail. FIG. 2A shows the distal end of the sheath 102, in which the retrieval assembly 104 is in its collapsed position. In this collapsed position, the retrieval assembly 104 fits within the sheath 102, and may be advanced while collapsed within the sheath 102 into a position within a body.

FIG. 2B shows the retrieval assembly 104 partially extending from the distal end of the sheath 102, to expose a portion of the retrieval assembly 104, placing the retrieval assembly 104 in the first position. In this first position, prongs 200a-200c of the retrieval assembly 104 form an open ended grasper configuration that may be used to grasp objects such as stones or calculi. An operator retracts the retrieval assembly 104 slightly, either by moving the retrieval assembly 104 or by moving the sheath 102, to cause the prongs 200a-200c to move closer to each other, thereby closing the grasper. The operator extends the retrieval assembly 104 slightly, either by moving the retrieval assembly 104 or by moving the sheath 102, to cause the prongs 200a-200c to separate, thereby opening the grasper. Actuation of the medical retrieval device 100 over a range up to, and slightly beyond the first position permits the retrieval assembly 104 to operate as a grasper.

As can be seen, in this illustrative embodiment, the prongs 200a-200c have a generally curved shape when the retrieval assembly 104 is in the first position. This curved shape may assist in grasping objects within the prongs 200a-200c.

FIG. 2C shows the retrieval assembly 104 fully extended from the distal end of the sheath 102, to expose substantially the entire retrieval assembly 104, placing the retrieval assembly 104 in the second position. In this second position, the prongs 200a-200c form a substantially close ended configuration that may enclose objects such as stones or calculi within a basket formed by the prongs 200a-200c. Advantageously, since the tips of the prongs 200a-200c are not connected to each other, an object may be released from the basket formed by the prongs 200a-200c by separating the ends of the prongs 200a-200c. An operator may release an object from the retrieval assembly 104 by actuating the medical device 100 to partially retract the retrieval assembly 104, either by moving the retrieval assembly 104, or by moving the sheath 102. Additionally, an object caught within the basket formed by the prongs 200a-200c may apply a predetermined force (i.e. sufficient force to separate at least one of the prongs 200a-200c from the others), to open the distal end of the basket formed by the prongs 200a-200c, thereby releasing the captured material.

In the second position, the distal portions of the prongs 200a-200c, which extended from the sheath 102 when the retrieval assembly 104 was in the first position have reversed their orientation, and have a shape that curves generally inward. This inward-curving shape causes the distal end of the basket formed by the prongs 200a-200c to have a narrow configuration.

As can be seen in FIGS. 2A-2C, the ends of the prongs 200a-200c comprise barbs 202a-202c. When the retrieval assembly 104 is in the first position, these barbs point generally inward, towards a central or longitudinal axis 202 of the retrieval assembly 104. In this configuration, the barbs 202a-202c may enhance the ability of the retrieval assembly 104 to act as a grasper, by catching on material held by the prongs 200a-200c.

When the retrieval assembly 104 is in the second position, the barbs 202a-202c point outward, away from the longitudinal axis 202 of the retrieval assembly 104. In this configuration, the barbs 202a-202c do not interfere with the basket operation of the retrieval assembly 104, and will not prevent objects from being released from the basket formed by the prongs 200a-200c.

It will be understood that alternative embodiments of the retrieval assembly 104 having a greater number of prongs can be constructed, and that the selection of three prongs in the retrieval assembly 104 is for illustrative purposes only. Embodiments of a retrieval assembly for use with the present invention will typically have either three or four prongs, though configurations having a greater number of prongs are within the scope of the invention.

The retrieval assembly 104, including the prongs 200a-200c, may be produced in a variety of materials, including, but not limited to nitinol, stainless steel, Co—Cr alloys, and titanium alloys. The retrieval assembly 104 may be formed as a single unit or by assembling the prongs 200a-200c.

Figure 3A:
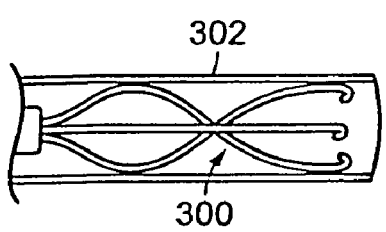
FIGS. 3A-C show a second embodiment of a retrieval assembly in accordance with the invention in a collapsed position, a first position, and a second position, respectively.
Figure 3B:
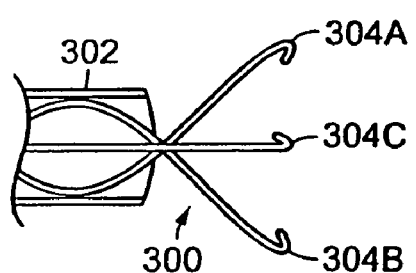
Figure 3C:
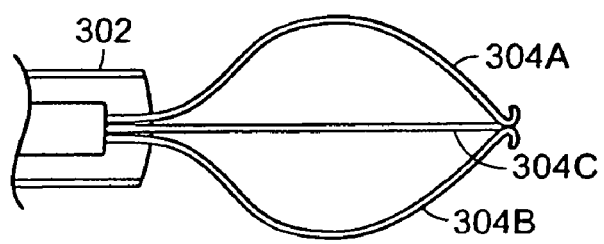

Referring now to FIGS. 3A-3C, a second illustrative embodiment of a retrieval assembly for use with the medical device of the present invention is described. In FIG. 3A, a retrieval assembly 300 is in a collapsed position within a distal end of a sheath 302.

FIG. 3B shows the retrieval assembly 300 partially extending from the distal end of the sheath 302, so that a portion of the retrieval assembly 300 is exposed, placing the retrieval assembly 300 in the first position. In this first position, prongs 304a-304c of the retrieval assembly 300 form an open configuration that may be used to grasp objects such as stones or calculi. An operator can slightly retract or extend the retrieval assembly 300 (either by moving the retrieval assembly 300 or by moving the sheath 302) to cause the prongs 304a-304c to move closer to each other, thereby closing the grasper, or to separate farther from each other, thereby opening the grasper. Actuation of the device over a range up to, and slightly beyond the first position permits the retrieval assembly 300 to operate as a grasper.

In this embodiment, the distal ends of the prongs 304a-304c that extend from the sheath 302 when the retrieval assembly 300 is in the first position have a generally linear shape. This shape is determined, in part, by the shape of the basket that will be formed by the prongs 304a-304c when the retrieval assembly is more fully extended.

FIG. 3C shows the retrieval assembly 300 fully extended from the distal end of the sheath 302, to expose substantially the entire retrieval assembly 300, placing the retrieval assembly 300 in the second position. In this second position, the prongs 304a-304c form a substantially closed configuration that may enclose objects such as stones or calculi within a basket formed by the prongs 304a-304c. As in other embodiments, since the tips of the prongs 304a-304c are not connected to each other, an object may be released from the basket formed by the prongs 304a-304c by separating the ends of the prongs 304a-304c. An operator may release an object from the retrieval assembly 300 by partially retracting the retrieval assembly 300, either by moving the retrieval assembly 300 or by moving the sheath 302. Additionally, an object caught within the basket formed by the prongs 304a-304c may apply a predetermined force sufficient to separate at least one of the prongs 304a-304c from the others, permitting the object to escape.

Because of the generally linear shape of the distal ends of the prongs 304a-304c, the basket formed by the prongs 304a-304c when the retrieval assembly 300 is in the second position has a generally convex form.

Figure 4A:
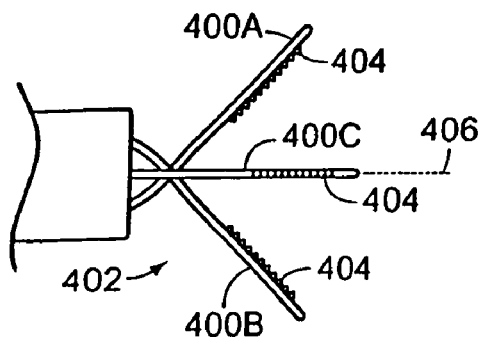
FIGS. 4A-B show an embodiment of a retrieval assembly in accordance with the invention, wherein distal portions of prongs of the retrieval assembly include a series of teeth.
Figure 4B:
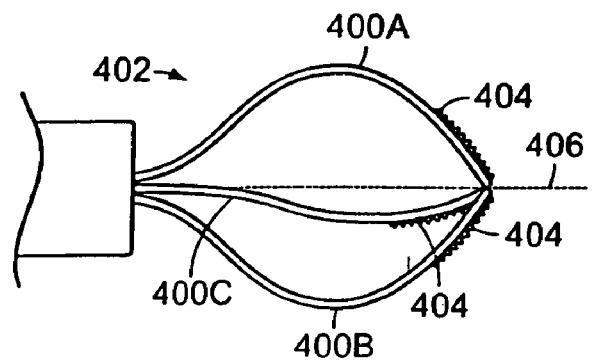

Referring to FIGS. 4A-4B, an alternative design for the distal portions of the prongs of a retrieval assembly for use with the medical device of the present invention is described. Each of prongs 400a-400c of a retrieval assembly 402 includes a series of teeth 404. As shown in FIG. 4A, when the retrieval assembly 402 is in the first position, being used as a grasper, the teeth 404 face inward, towards a longitudinal axis 406 of the retrieval assembly 402. In this configuration, the teeth 404 enhance the ability of the retrieval assembly 402 to grasp objects such as stones or calculi, and may prevent objects from being inadvertently released from the grasper formed by the prongs 400a-400c.

As shown in FIG. 4B, when the retrieval assembly 402 is in the second position, configured as a basket-type retrieval device, the teeth 404 face outward, away from the longitudinal axis 406 of the retrieval assembly 402. Because the teeth 404 face outward, they will not interfere with the ability of the retrieval assembly 402 to release objects from the basket formed by the prongs 400a-400c. Additionally, because the teeth 404 are disposed on distal portions of the prongs 400a-400c that do not typically come into contact with tissue during retrieval of an object, the teeth 404 are unlikely to cause damage to tissue during the retrieval of an object.

The teeth 404 may be formed on the distal portions of the prongs 400a-400c through a variety of techniques, including etching, cutting, or being formed or molded when a prong is formed or molded. The number of teeth, their shapes, and the extent of the distal portion of the prongs 400a-400c over which the teeth extend may vary in alternative embodiments. Additionally, alternative embodiments of the retrieval assembly 402 wherein the teeth 404 are formed on one or more of the prongs 400a-400c, but not necessarily on all of the prongs 400a-400c may be constructed.

Figure 5A:
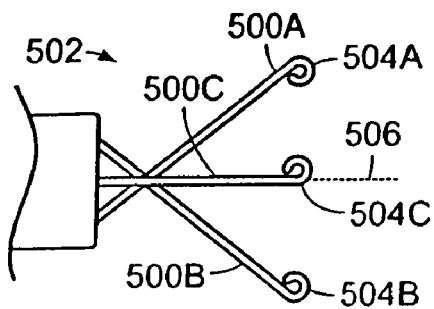
FIGS. 5A-B show an embodiment of a retrieval assembly in accordance with the invention, wherein prongs of the retrieval assembly have rolled tips.
Figure 5B:
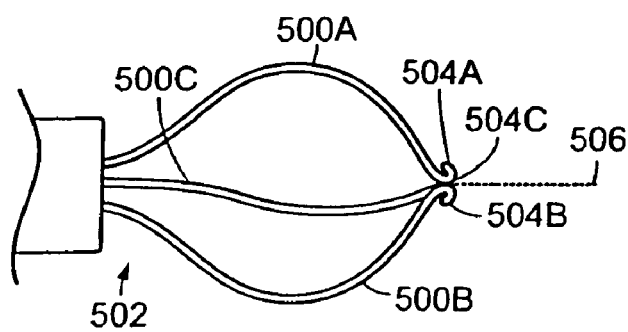

FIGS. 5A and 5B show an alternative embodiment of a retrieval assembly for use with the medical device of the present invention, in which prongs 500a-500c have rolled tips, rather than barbed tips, as shown in previous embodiments. In FIG. 5A, a retrieval assembly 502 is in the first position, for use as a grasper. Rolled tips 504a-504c of the prongs 500a-500c point generally inward, towards a central or longitudinal axis 506 of the retrieval assembly 502. In this configuration, the rolled tips 504a-504c may assist in grasping material between the prongs 500a-500c.

When the retrieval assembly 502 is in the second position, the rolled tips 504a-504c point outward, away from the longitudinal axis 506 of the retrieval assembly 502, so they do not interfere with the operation of the retrieval assembly 502 as a basket-type retrieval device. Advantageously, the rolled tips 504a-504c will not catch on tissue, such as the side of the ureter, when a stone or other material is released from the basket formed by the prongs 500a-500c by applying a force to separate the prongs.

It will be understood by one skilled in the art that other configurations for the ends or tips of the prongs of a retrieval assembly for use with the medical device of the present invention are possible. For example, the tips may be rounded, spiral-shaped, ball-tipped, or may have other shapes or configurations.

Referring now to FIGS. 6A-6D, a method of using the medical device of the present invention as a grasper is described. Typically, an operator inserts a distal portion of the device into a body tract, such as the ureter of a patient, using an endoscope or guidewire. The operator typically views the progress of the operation through fluoroscopy, though other viewing methods may be used.

Figure 6A:
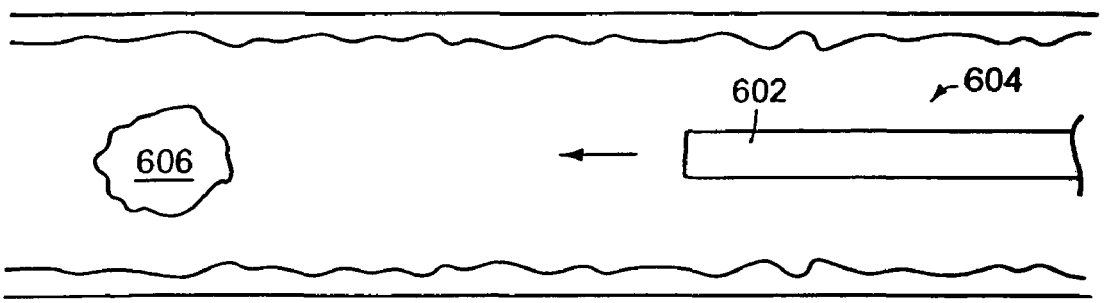
FIGS. 6A-D illustrate a method of using a medical retrieval device in accordance with the invention as a grasper.
Figure 6B:
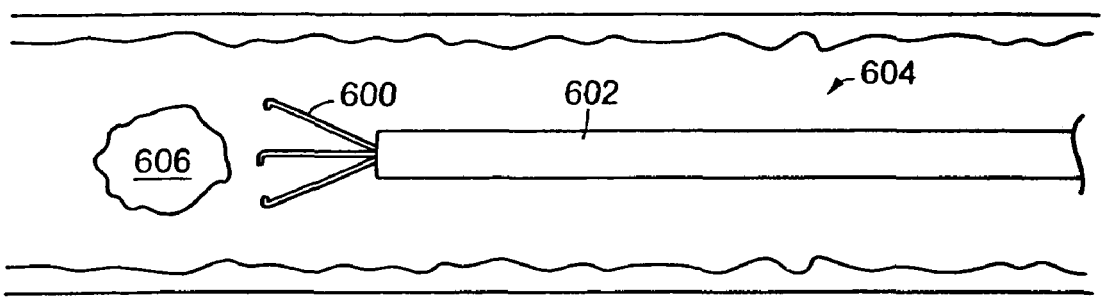
Figure 6C:
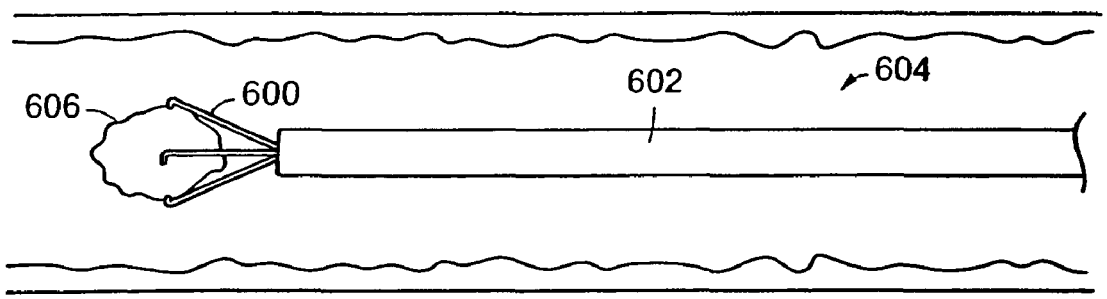
Figure 6D:
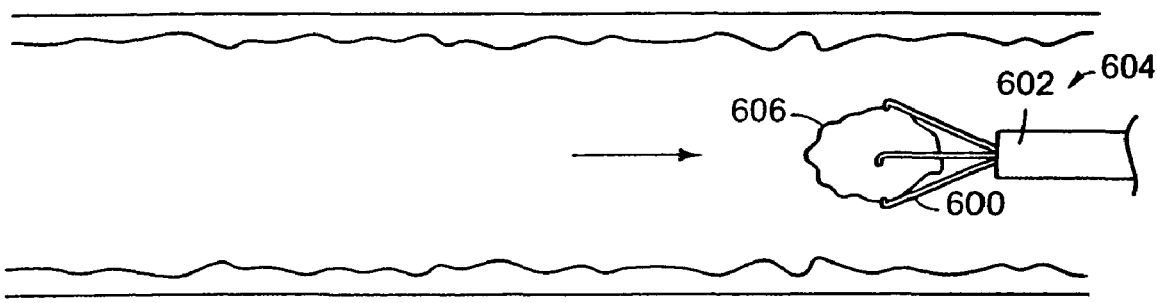

As shown in FIG. 6A, with the retrieval assembly in the collapsed position within a sheath 602, the operator maneuvers a distal portion of a medical device 604 into position near a stone 606 that is to be retrieved or manipulated. When the distal portion of the medical device 604 approaches the stone 606, the operator actuates the medical device 604 to place a retrieval assembly 600 in the first position, to use the retrieval assembly 600 as a grasper, as shown in FIG. 6B. As shown in FIG. 6C, the operator maneuvers the retrieval assembly 600 so that the prongs of the retrieval assembly 600 encompass at least a portion of the stone 606. As shown in FIG. 6D, the operator then actuates medical device 604 to cause the prongs of the retrieval assembly 600 to close, thereby grasping a front portion of the stone 606. Once the stone 606 is grasped in the prongs of the retrieval assembly 600, it may be retrieved or maneuvered. To release the stone 606, the operator may actuate the medical device 604 to cause the prongs of the retrieval assembly 600 to open, releasing the stone 606.

Figure 7A:
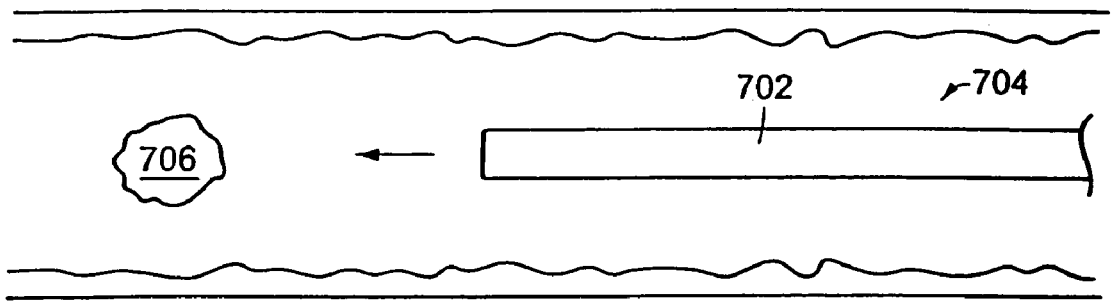
FIGS. 7A-C illustrate a method of using a medical retrieval device in accordance with the invention as a basket-type retrieval device.
Figure 7B:
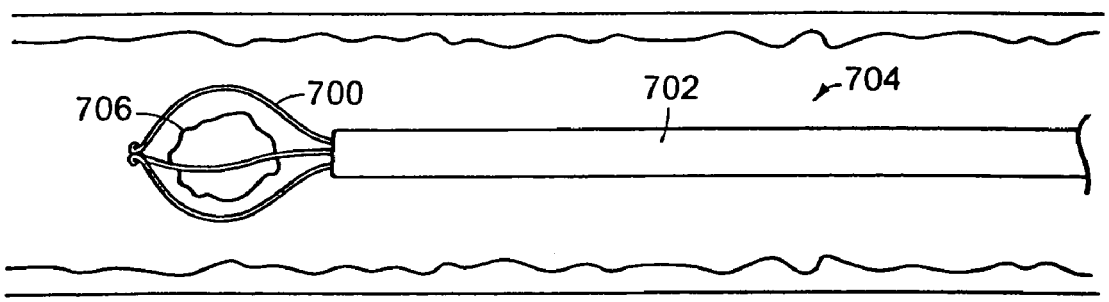
Figure 7C:
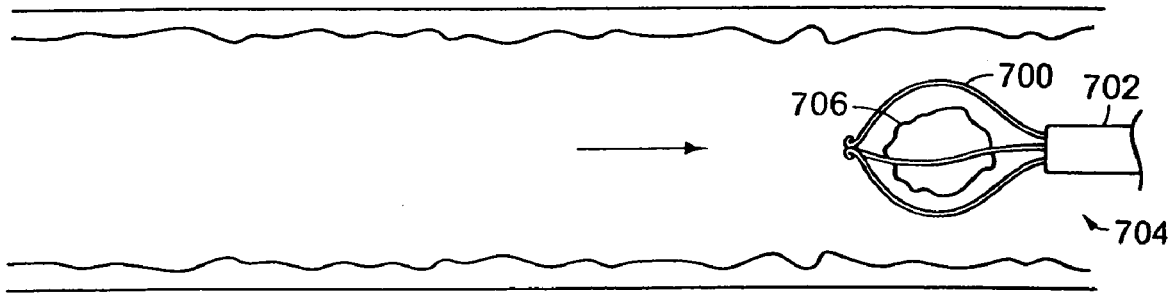

FIGS. 7A-7C show an illustrative example of a method of using the medical device of the present invention as a retrieval basket. In FIG. 7A, the operator maneuvers a distal portion of a medical device 704, into position near a stone 706. During insertion of the medical device 704 and maneuvering of the medical device 704 into position, a retrieval assembly is typically kept in a collapsed position within the sheath 702.

When the distal portion of the medical device 704 approaches a stone 706, the operator actuates the medical device 704 to place a retrieval assembly 700 in the second position, to use the retrieval assembly 700 as a basket-type retrieval device, as shown in FIG. 7B. Generally, the operator may capture the stone 706 by placing the retrieval assembly 700 in the second position and then maneuvering the retrieval assembly 700 around the stone 706 until the stone 706 passes between the prongs of the retrieval assembly 700, and into the basket formed by the prongs of the retrieval assembly 700.

As shown in FIG. 7C, once the stone 706 is captured in the basket formed by the prongs of the retrieval assembly 700, the medical device 704, along with the retrieval assembly 700 (which remains in the second position), and the captured stone 706 may be withdrawn from the body. If it becomes necessary to release the stone 706, the operator may actuate the medical device 704 to cause the prongs of the retrieval assembly 700 to separate, thereby releasing the stone 706.

Figure 8A:
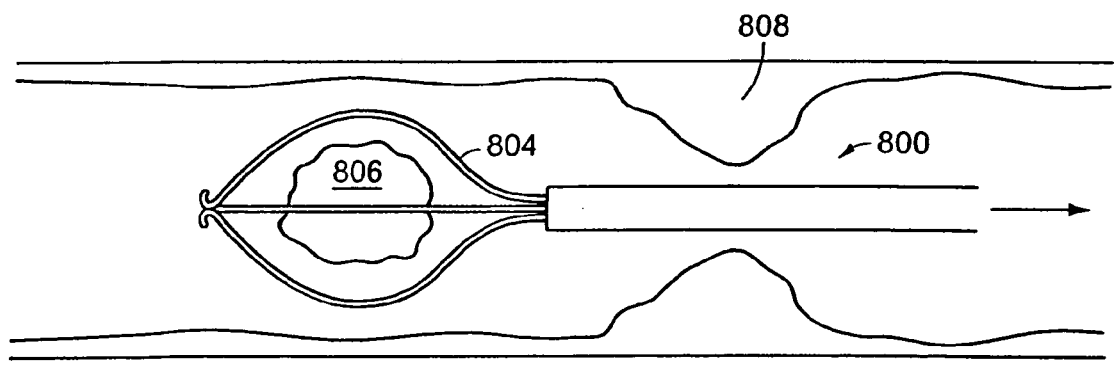
FIGS. 8A-B illustrate the release of material from a medical device in accordance with the invention when a stricture through which the material is unable to pass is encountered.
Figure 8B:
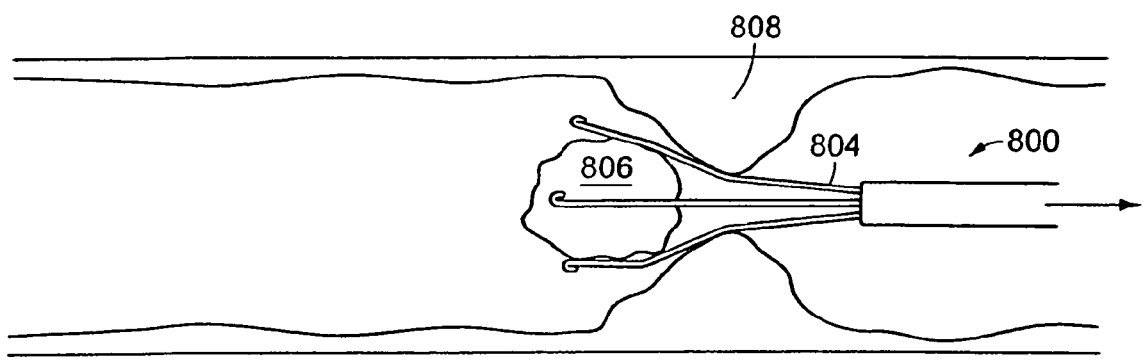

As shown in FIGS. 8A-8B, since the prongs of the retrieval assembly are deformable, and are not connected at their distal ends when the retrieval assembly is configured as a basket-type retrieval device, a captured stone may be released when a stricture is encountered through which the stone cannot pass. Advantageously, this may prevent tissue damage that would be caused by attempting to force a stone through such a stricture.

In FIG. 8A, a medical device 800, including a retrieval assembly 804 has captured a stone 806 in a basket formed by the prongs of the retrieval assembly 804 when the retrieval assembly 804 is in the second position. The medical device 800 is in the process of being withdrawn from the patient, but will encounter a stricture 808, which is too small to permit the stone 806 to pass.

As shown in FIG. 8B, when the stricture 808 is encountered, the stone 806 is unable to pass, and exerts force on a distal portion of the prongs of the retrieval assembly 804. Because the distal tips of the retrieval assembly 804 are not connected or otherwise held together, when this force exceeds a predetermined force (i.e. a force sufficient to cause one or more prongs of the retrieval assembly 804 to separate), one or more of the prongs of the retrieval assembly 804 will separate, releasing the stone 806.

Other embodiments incorporating the concepts disclosed herein are within the spirit and scope of the invention. The described embodiments are illustrative of the invention and not restrictive.

What is claimed is:

1. A medical retrieval device, comprising:
 a sheath including a distal end; and
 a retrieval assembly including a longitudinal axis and a plurality of prongs, wherein a longitudinal movement of the retrieval assembly from within the distal end of the sheath forms an open grasper-like configuration and a substantially closed basket-like configuration of the retrieval assembly and causes a portion of at least one prong of the plurality of prongs to move from one side of the longitudinal axis to an opposite side of the longitudinal axis, the basket-like configuration being a configuration in which substantially an entire length of a prong outside the sheath extends on only one side of the longitudinal axis, such that the length of the prong outside the sheath does not cross the longitudinal axis.

2. The medical device of claim 1, wherein the retrieval assembly changes from the grasper-like configuration to the basket-like configuration as the retrieval assembly is extended from the distal end of the sheath.

3. The medical device of claim 1, wherein;
 in the grasper-like configuration, each prong of the plurality of prongs diverges from each other in a distal portion to form an open grasper, and in the basket-like configuration, each prong of the plurality of prongs converges towards each other in the distal portion to form a closed basket.

4. The medical device of claim 1, wherein the retrieval assembly includes a barb on a distal-most region of at least one prong of the plurality of prongs.

5. The medical device of claim 4, wherein the barb is positioned on a tip of the at least one prong.

6. The medical device of claim 4, wherein,
in the grasper-like configuration, the barb curves towards the longitudinal axis, and
in the basket-like configuration the barb curves away from the longitudinal axis.

7. The medical device of claim 6, wherein the barb transforms from curving toward the longitudinal axis to curving away from the longitudinal axis as the retrieval assembly extends from the sheath.

8. The medical device of claim 1, wherein the retrieval assembly further includes a collapsed configuration when the retrieval assembly is within the sheath, the collapsed configuration being a configuration in which each prong of the plurality of prongs cross from one side of the longitudinal axis to an opposite side of the longitudinal axis.

9. A medical device comprising:
an elongate sheath; and
a retrieval assembly having a longitudinal axis and a plurality of prongs, the retrieval assembly being configured to transform from a collapsed configuration within the sheath to an open grasper-like configuration and to a substantially closed basket-like configuration,
the collapsed configuration being a configuration in which at least one prong of the plurality of prongs extends from one side of the longitudinal axis to an opposite side of the longitudinal axis, and
the basket-like configuration being a configuration in which substantially an entire length of the one prong outside the sheath extends on only one side of the longitudinal axis, such that the length of the one prong outside the sheath does not cross the longitudinal axis.

10. The medical device of claim 9, wherein the grasper-like configuration is a configuration in which the plurality of prongs partially extend from the sheath, and the basket-like configuration is a configuration in which the plurality of prongs extends further from the sheath.

11. The medical device of claim 9, wherein the plurality of prongs are coupled to each other at one end and uncoupled to each other at an opposite end.

12. The medical device of claim 11, wherein the grasper-like configuration is a configuration in which the retrieval assembly is configured to grasp an object between the plurality of prongs at the opposite end, and the basket-like configuration is a configuration in which the retrieval assembly is configured to enclose the object within a basket formed by the plurality of prongs.

13. The medical device of claim 9, wherein the retrieval assembly includes a barb on a tip of at least one prong of the plurality of prongs, the barb curving towards the longitudinal axis when the retrieval assembly is in the grasper-like configuration and curving away from the longitudinal axis when the retrieval assembly is in the basket-like configuration.

14. The medical device of claim 9, wherein the retrieval assembly includes one or more teeth proximate a tip of at least one prong of the plurality of prongs.

15. The medical device of claim 14, wherein the tip faces the longitudinal axis when the retrieval assembly is in the grasper-like configuration, and the tip faces away from the longitudinal axis when the retrieval assembly is in the basket-like configuration.

16. A medical device comprising:
an elongate sheath;
a retrieval assembly having a longitudinal axis and a plurality of prongs, the retrieval assembly being configured to transform from a collapsed configuration within the sheath first to an open grasper-like configuration and then to a substantially closed basket-like configuration as the retrieval assembly is extended outside the sheath, the collapsed configuration being a configuration in which at least one prong of the plurality of prongs extends from one side of the longitudinal axis to an opposite side of the longitudinal axis; and
a barb positioned on a distal tip of the one prong, the barb curving towards the longitudinal axis when the retrieval assembly is in the grasper-like configuration and curving away from the longitudinal axis when the retrieval assembly is in the basket-like configuration.

17. The medical device of claim 16, wherein the grasper-like configuration and the basket-like configuration are configurations in which substantially an entire length of the one prong outside the sheath extends only on one side of the longitudinal axis, such that the length of the one prong outside the sheath does not cross the longitudinal axis.

18. The medical device of claim 16, wherein the grasper-like configuration is a configuration in which distal ends of each prong of the plurality of prongs approach the longitudinal axis to grasp an object between the plurality of prongs as the retrieval assembly is further extended outside the sheath.

19. The medical device of claim 16, wherein substantially an entire length of a portion of a prong outside the sheath has a concave shape relative to the longitudinal axis when the retrieval assembly is in the open grasper-like configuration, and wherein the entire length of the portion of the prong has a convex shape relative to the longitudinal axis when the retrieval assembly transforms from the grasper-like configuration to the basket-like configuration.

* * * * *